(12) United States Patent
Ito

(10) Patent No.: US 6,482,164 B2
(45) Date of Patent: Nov. 19, 2002

(54) AUTOMATIC BLOOD PRESSURE MEASURING APPARATUS

(75) Inventor: Hisashi Ito, Komaki (JP)

(73) Assignee: Colin Corporation, Aichi-ken (JP)

( * ) Notice: Subject to any disclaimer, the term of this patent is extended or adjusted under 35 U.S.C. 154(b) by 0 days.

(21) Appl. No.: 09/778,790

(22) Filed: Feb. 8, 2001

(65) Prior Publication Data

US 2001/0020133 A1 Sep. 6, 2001

(30) Foreign Application Priority Data

Mar. 6, 2000 (JP) ........................................ 2000-060291

(51) Int. Cl.[7] .............................. A61B 5/02; A61B 5/00
(52) U.S. Cl. ...................... 600/483; 600/304; 600/490; 600/588
(58) Field of Search ................................ 600/300, 301, 600/304, 481, 483–485, 490–504, 551, 588; 128/897, 898, 900, 920

(56) References Cited

U.S. PATENT DOCUMENTS 5,564,427 A * 10/1996 Aso et al. ................... 600/494
6,093,151 A * 7/2000 Shine et al. ................. 600/485
6,302,849 B1 * 10/2001 Shine et al. ................. 600/485

* cited by examiner

Primary Examiner—Kevin Shaver
Assistant Examiner—Charles Marmor, II
(74) Attorney, Agent, or Firm—Oliff & Berridge, PLC

(57) ABSTRACT

An apparatus for automatically measuring a blood pressure of a female subject, including a blood-pressure measuring device which includes an inflatable cuff adapted to apply a pressing force to a body portion of the subject and automatically measures, by changing the pressing force of the cuff, a blood pressure of the female subject at a predetermined measurement period, a labor-pain-signal detecting device which detects, from the female subject, a labor-pain signal which changes in relation to a labor pain of the subject, and a blood-pressure-measurement starting device for operating the blood-pressure measuring device to start a blood-pressure measurement, when the predetermined measurement period has elapsed and when the labor-pain signal detected by the labor-pain-signal detecting device falls within a reference range.

8 Claims, 4 Drawing Sheets

AUTOMATIC BLOOD PRESSURE MEASURING APPARATUS

BACKGROUND OF THE INVENTION

1. Field of the Invention

The present invention relates to an automatic blood pressure measuring apparatus which can accurately measure a blood pressure of a female subject even at the time of childbirth.

2. Related Art Statement

There is known an automatic blood pressure (BP) measuring apparatus which monitors BP values of a living subject by periodically changing an air pressure of an inflatable cuff applied to a body portion of the subject at a predetermined measurement period and detecting a pressure pulse wave produced in the cuff during the change of air pressure of the cuff. It is known that the BP values measured using the inflatable cuff are reliable.

Meanwhile, it is medically important to monitor BP values of a female subject at the time of childbirth. However, in the case where the above-mentioned BP measuring apparatus is used to monitor, using the cuff, BP values of a female subject who heavily moves her body each time she feels a labor pain (i.e., uterine contraction), the BP measuring apparatus may not accurately measure the BP values of the subject because of her heavy physical motion.

SUMMARY OF THE INVENTION

It is therefore an object of the present invention to provide an automatic blood pressure measuring apparatus which can measure an accurate blood pressure of a female subject, even during childbirth.

The above object has been achieved by the present invention. According to a first feature of the present invention, there is provided an apparatus for automatically measuring a blood pressure of a female subject, comprising a blood-pressure measuring device which includes an inflatable cuff adapted to apply a pressing force to a body portion of the subject and automatically measures, by changing the pressing force of the cuff, a blood pressure of the female subject at a predetermined measurement period; a labor-pain-signal detecting device which detects, from the female subject, a labor-pain signal which changes in relation to a labor pain of the subject; and a first blood-pressure-measurement starting means for operating the blood-pressure measuring device to start a blood-pressure measurement, when the predetermined measurement period has elapsed and when the labor-pain signal detected by the labor-pain-signal detecting device falls within a reference range.

In the present automatic BP measuring apparatus, the first BP-measurement starting means operates the BP measuring device to start a BP measurement, only when the labor-pain signal detected by the labor-pain-signal detecting device falls within a reference range. If the labor-pain signal falls within the reference range, then the female subject is not feeling a labor pain and accordingly she is not moving her body. Since the present apparatus starts a BP measurement when the female subject is not moving her body, it can accurately measure one or more BP values of the subject.

According to a second feature of the present invention, the blood-pressure measuring apparatus further comprises a labor-pain-period-relating-information determining means for determining, based on the labor-pain signal detected by the labor-pain-signal detecting device, labor-pain-period-relating information relating to a labor-pain period at which the female subject periodically feels a labor pain; and a measurement-period shortening means for shortening the predetermined measurement period, when the determined labor-pain-period-relating information indicates that the labor-pain period of the subject has shortened.

During childbirth, it is medically needed to detect more quickly any abnormal tendency of the female subject when the labor-pain-period-relating information indicates that the labor-pain period of the subject has shortened. To this end, the present automatic BP measuring apparatus employs the measurement-period shortening means which shortens, when the labor-pain-period-relating information indicates that the labor-pain period of the subject has shortened, the predetermined measurement period, so that the BP measuring device measures a BP value of the subject at the shortened measurement period. Thus, the present apparatus can more quickly detect the abnormal tendency of BP values of the female subject.

According to a third feature of the present invention, the blood-pressure measuring apparatus further comprises an abnormality judging means for judging, when the labor-pain signal detected by the labor-pain-signal detecting device does not fall within the reference range when the blood-pressure measuring device is performing a first blood-pressure measurement, that the first blood-pressure measurement is abnormal; and a second blood-pressure-measurement starting means for operating the blood-pressure measuring device to start a second blood-pressure measurement when the labor-pain signal detected by the labor-pain-signal detecting device has changed to fall within the reference range again after the abnormality judging means has judged that the first blood-pressure measurement is abnormal.

When the female subject feels a labor pain during a BP measurement of the BP measuring device, the BP measuring device may not accurately measure one or more BP values of the subject. However, the present automatic BP measuring apparatus employs the abnormality judging means which judges, if the labor-pain signal does not fall within the reference range when the BP measuring device is performing a first BP measurement, that the first BP measurement is abnormal, and the second BP-measurement starting means which operates the BP measuring device to start a second BP measurement when the labor-pain signal has changed to fall within the reference range again after the abnormality judging means has judged that the first BP measurement is abnormal. Thus, the present apparatus can accurately measure one or more BP values of the female subject.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
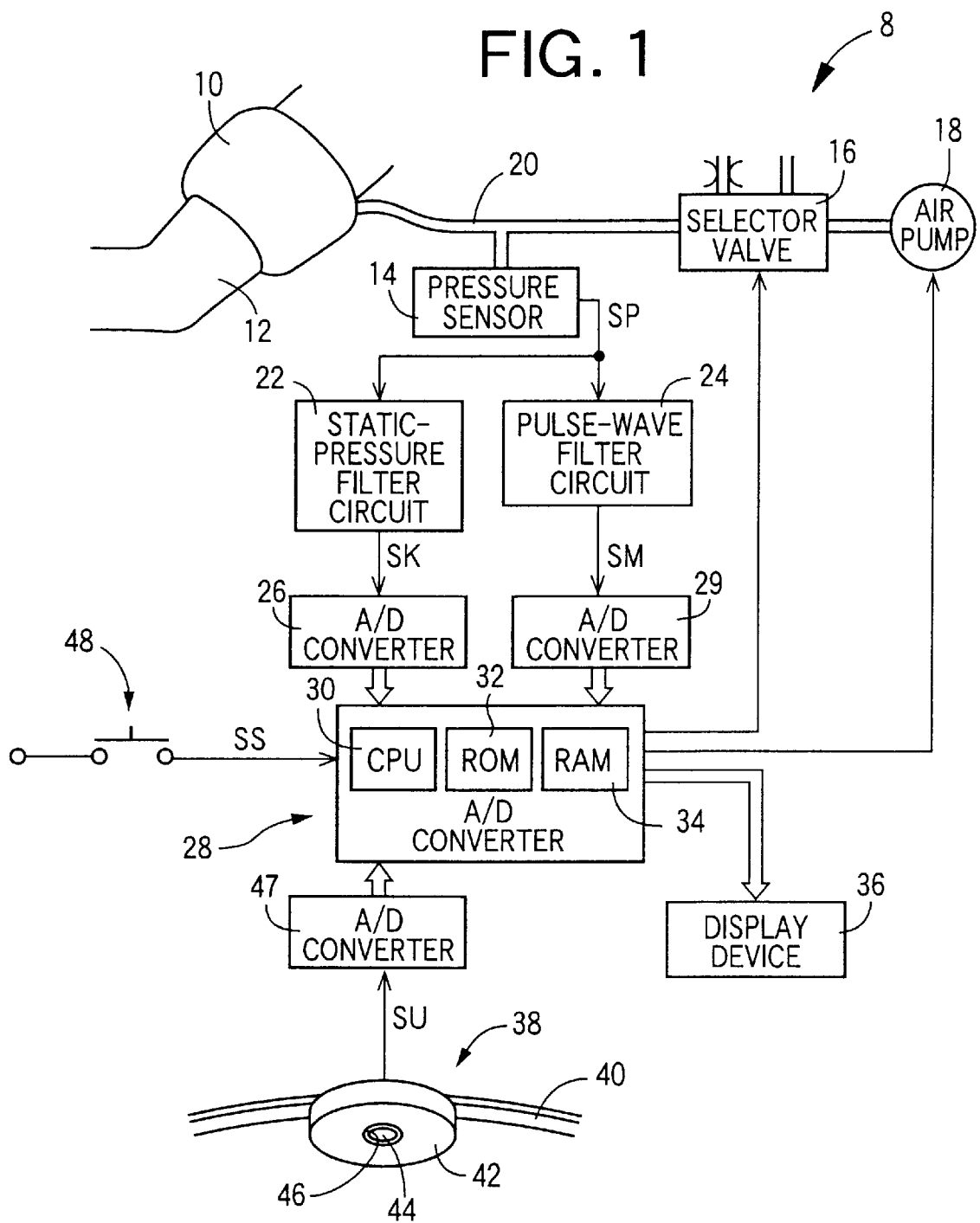
FIG. 1 is a diagrammatic view for explaining a construction of an automatic blood pressure measuring apparatus embodying the present invention.

Referring first to FIG. 1, there will be described an automatic blood pressure (BP) measuring apparatus 8 embodying the present invention.

In FIG. 1, the automatic BP measuring apparatus 8 includes an inflatable cuff 10 which has a belt-like cloth bag and an inflatable rubber bag accommodated in the cloth bag and which is adapted to be wound around an upper arm 12 of a female subject, and a pressure sensor 14, a selector valve 16, and an air pump 18 each of which is connected to the cuff 10 via a piping 20. The selector valve 16 is selectively placed in an inflation position in which the selector valve 16 permits pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representing the detected pressure, to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SK representing the static pressure Pc in the cuff 10. The cuff-pressure signal SK is supplied to a control device 28 via an analog-to-digital (A/D) converter 26.

The pulse-wave filter circuit 24 includes a band-pass filter and extracts, from the pressure signal SP, an oscillating component having predetermined frequencies, i.e., a pulse-wave signal SM. The pulse-wave signal SM is supplied to the control device 28 via an A/D converter 29. The pulse-wave signal SM represents a cuff pulse wave, i.e., an oscillatory pressure wave which is produced from a brachial artery (not shown) of the subject in synchronism with the heartbeat of the subject and is propagated to the cuff 10.

The control device 28 is provided by a so-called microcomputer including a central processing unit (CPU) 30, a read only memory (ROM) 32, a random access memory (RAM) 34 and an input-and-output (I/O) port (not shown). The CPU 30 processes signals according to the control programs pre-stored in the ROM 32 by utilizing the temporary-storage function of the RAM 34, and supplies drive signals to the selector valve 16 and the air pump 18 through the I/O port. Thus, the control device 28 controls the present BP measuring apparatus 8 to measure one or more blood pressure values BP of the female subject and display, on a display device 36, the measured blood pressure values BP of the subject. The display device 36 includes a CRT (cathode ray tube) or a LCD (liquid crystal display).

The present BP measuring apparatus 8 additionally includes, as a labor-pain-signal detecting device, a well-known external tocodynamometer 38 which functions as a contact element; and a fastening band 40 for fastening the tocodynamometer 38 on an appropriate portion of the abdomen of the female subject. The tocodynamometer 38 includes a disc-like guard ring 42, and a pressure sensing element 44 which is fitted in a central hole 46 formed in a central portion of a contact surface of the guard ring 42 that is adapted to contact the abdomen of the subject. The diameter of the central hole 46 is somewhat larger than that of the pressure-sensing element 44. In a state in which the tocodynamometer 38 is held in pressed contact with the abdomen of the female subject with the help of the fastening band 40, the pressure-sensing element 44 detects, via the abdomen, a pressure produced when the uterus of the subject contracts and hardens.

The tocodynamometer 38 produces a labor-pain signal SU representing the pressure detected by the pressure-sensing element 44, and supplies the labor-pain signal SU to the control device 28 via an A/D converter 47. In addition, the control device 28 is supplied with a start/stop signal SS from a START/STOP button 48.

Figure 2:
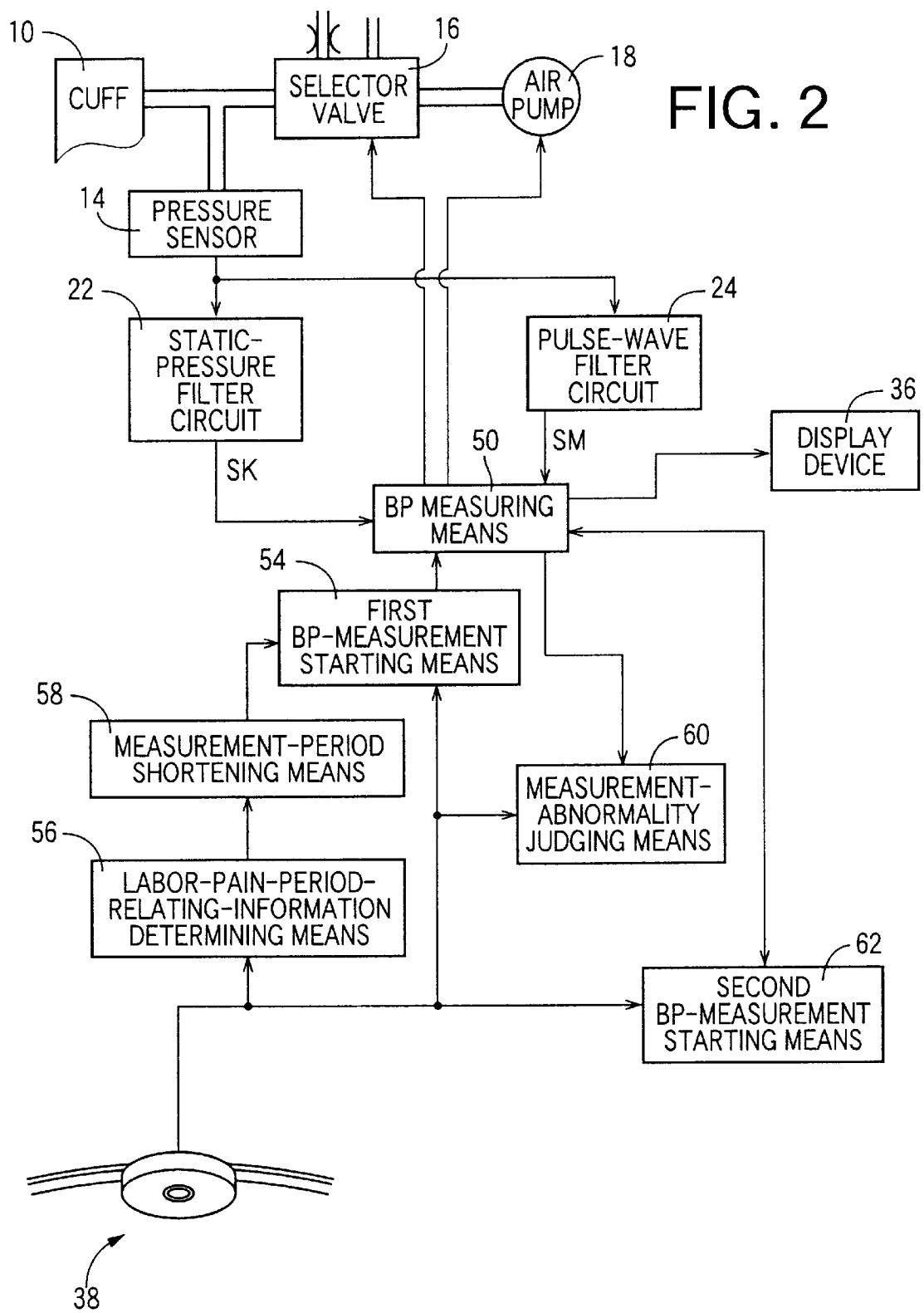
FIG. 2 is a block diagram for explaining essential functions of a control device of the apparatus of FIG. 1.

FIG. 2 illustrates essential functions of the control device 28 of the present BP measuring apparatus 8. In the figure, a BP measuring means 50 automatically controls, at a predetermined measurement period $T_{B1}$, the air pump 18 and the selector valve 16 to increase quickly the pressing pressure Pc of the cuff 10, represented by the cuff-pressure signal SK, up to a predetermined target value $P_{CM}$ (e.g., 180 mmHg) and subsequently decrease slowly the pressure Pc from the target value $P_{CM}$, at the rate of about 3 mmHg/sec, and measures one or more blood pressure values BP of the subject, based on variation of respective amplitudes of heartbeat-synchronous pulses of the pulse wave obtained during the slow deflation of the cuff 10. For example, the BP measuring means 50 determines a systolic, a mean, and a diastolic blood pressure value $BP_{SYS}$, $BP_{MEAN}$, $BP_{DIA}$ of the subject, according to a well-known oscillometric method, based on variation of respective amplitudes of respective pulses of the pulse wave represented by the pulse-wave signal SM obtained while the pressure Pc of the cuff 10 is slowly decreased from the target value $P_{CM}$, at the rate of about 3 mmHg/sec, and operates the display device 36 to display the thus determined blood pressure values $BP_{SYS}$, $BP_{MEAN}$, $BP_{DIA}$.

A first BP-measurement starting means 54 operates the BP measuring means 50 to start a BP measuring operation, when the predetermined BP-measurement period $T_{B1}$ has elapsed and simultaneously when the labor-pain signal SU supplied from the tocodynamometer 38 falls within a predetermined reference range $R_B$. The BP measuring means 50 cannot measure accurate blood pressure values BP of the female subject in a state in which her physical motion is at a high level. When she feels a labor pain, her physical motion must be at the high level. Therefore, even when the BP-measurement period $T_{B1}$ has elapsed, the first BP-measurement starting means 54 does not operate or start the BP measuring means 50, when the labor-pain signal SU does not fall within the reference range $R_B$. The reference range $R_B$ means a predetermined small-width range around a predetermined base line L of tocodynagraphic waveform shown in FIG. 1. Thus, the reference range $R_B$ is used to judge whether or not the female subject is currently in a physical state in which she does not feel a labor pain. For example, the first BP-measurement starting means 54 judges whether the magnitude itself (i.e., voltage of electric signal) of labor-pain signal SU supplied from the tocodynamometer 38 falls within the predetermined reference range $R_B$. Alternatively, the first starting means 54 may be operated in such a manner that when an absolute value of a change value (e.g., a change rate or a change amount) of the magnitude of each data point of the labor-pain signal SU is not greater than a predetermined small value α, the first starting means 54 judges that the labor-pain signal SU falls within the reference range $R_B$. The change rate $d_{SU}$ of the magnitude of each current data point of the labor-pain signal SU may be a ratio of the magnitude of the each current data point of the signal SU to the magnitude of the preceding data point of the same SU. If the thus determined change rate $d_{SU}$ is not greater than the small value α, the first starting means 54 judges that the labor-pain signal SU falls within the reference range $R_B$. Alternatively, the first starting means 54 may be one which determines a base line L of tocodynagraphic waveform, based on the change value of the magnitude of each current data point of the labor-pain signal SU, and determines a reference range $R_B$, based on the thus determined base line L, such that the reference range $R_B$ has its lower limit $L_L$ equal to the base line L ($L_L$=L) and its upper limit $L_U$ equal to the base line L plus a predetermined value β ($L_U$=L+β). The predetermined BP-measurement period $T_{B1}$ may be 30 minutes.

Figure 3:
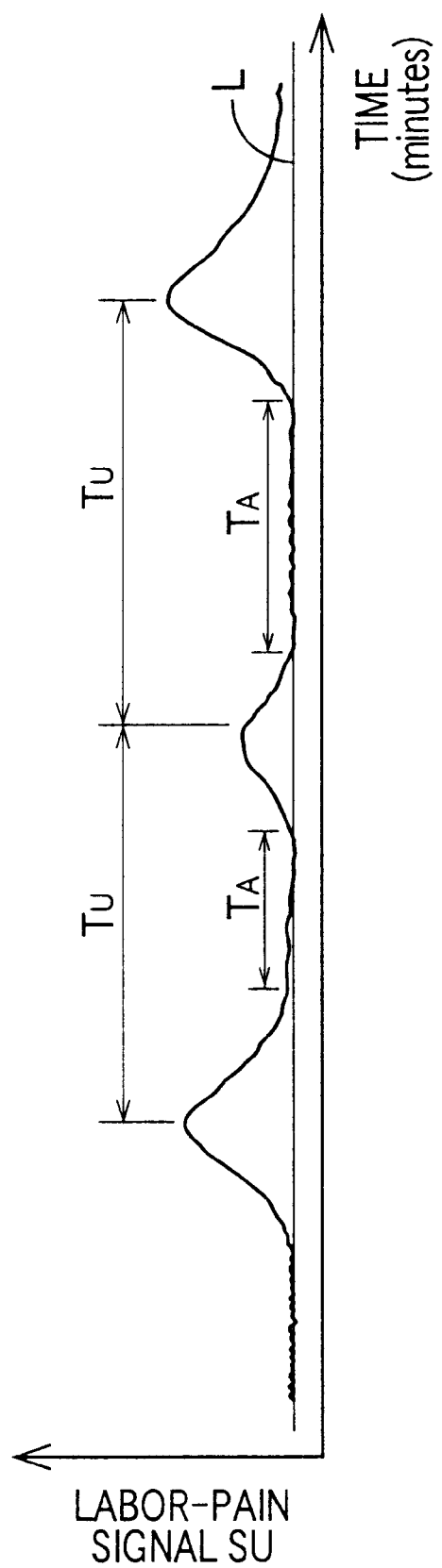
FIG. 3 is a view showing a tocodynagraphic waveform represented by a tocodynagraphic or labor-pain signal, SU, produced by a tocodynamometer employed in the apparatus of FIG. 1.

A labor-pain-period-relating-information determining means 56 determines, based on the labor-pain signal SU supplied from the tocodynamometer 38, a labor-pain-period-relating information relating to a labor-pain period at which the female subject feels labor pains. The labor-pain-period-relating information may be a labor-pain period $T_U$, or a no-pain period $T_A$ shown in FIG. 3. The labor-pain period $T_U$ may be determined as a time duration between respective maximum (or peak) values of two successive plateaus of the labor-pain signal SU that correspond to two successive labor-pain periods. The no-pain period $T_A$ may be determined as a time duration during which the labor-pain signal SU continues to fall within the reference range $R_B$.

A measurement-period shortening means 58 shortens the predetermined BP-measurement period $T_B$ to a shorter value, when the labor-pain-period-relating information determined by the labor-pain-period-relating-information determining means 56 indicates that the labor-pain period of the female subject has shortened. The measurement-period shortening means 58 may continuously shorten the predetermined BP-measurement period $T_B$ by respective amounts proportional to respective amounts of shortening of the labor-pain period of the subject. Alternatively, the shortening means 58 may stepwise, either one step or a plurality of steps, shorten the predetermined BP-measurement period $T_B$, by a predetermined incremental amount as the labor-pain period of the subject stepwise shortens.

A measurement-abnormality judging means 60 judges, when the labor-pain signal SU goes out of the reference range $R_B$ while the BP measuring means 50 is performing a BP measurement, that the BP measurement is abnormal, i.e., that the reliability or accuracy of one or more blood pressure values BP that would be measured in the BP measurement is low. Even if the BP measuring means 50 has started a BP measurement during the no-pain period $T_A$, the female subject may feel labor pains again during the BP measurement so that her physical motion may increase up to a high level. It can be estimated that the accuracy of blood pressure value or values BP of the subject measured in this state is low. Thus, the judging means 60 judges that the current BP measurement is abnormal.

A second BP-measurement starting means 62 operates, when the labor-pain signal SU has changed to fall within the reference range RB after the measurement-abnormality judging means 60 has judged that a first BP measurement is abnormal, the BP measuring means 50 to start a second BP measurement. When the measurement-abnormality judging means 60 judges that one or first BP measurement is abnormal, the female subject is feeling labor pains. Therefore, the BP measuring apparatus 8 waits for ending of the current labor-pain period and, when the next no-pain period $T_A$ starts, operates the BP measuring means 50 to start another or second BP measurement. The second BP measurement may be started immediately after the starting of the no-pain period $T_A$, or a predetermined duration of time after the starting of the period $T_A$.

Figure 4:
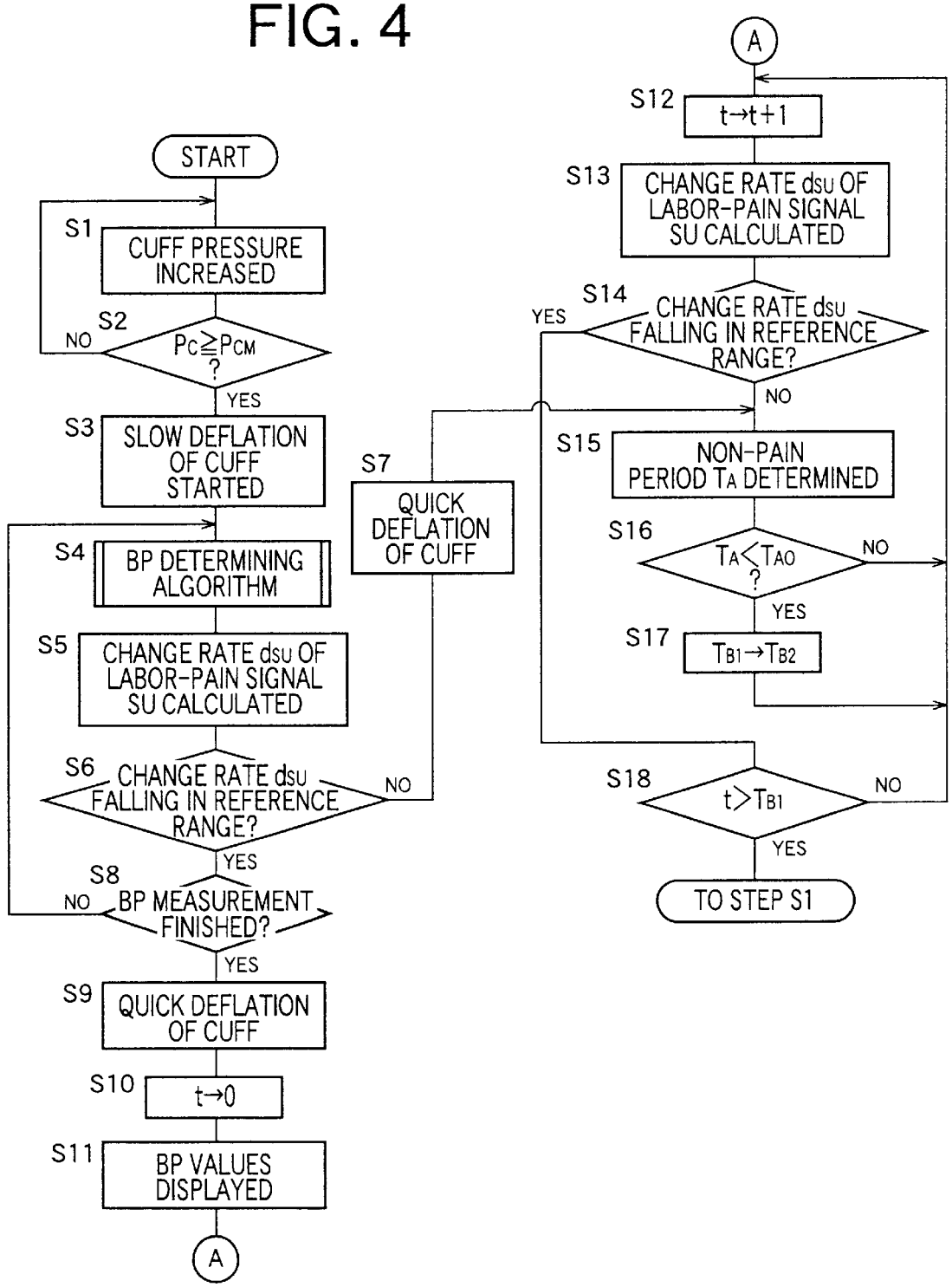
FIG. 4 is a flow chart representing a control program or routine according to which the control device of FIG. 2 controls the apparatus of FIG. 1.

Next, there will be described the operation of the control device 28 of the BP measuring apparatus 8 by reference to the flow chart of FIG. 4. The control program or routine represented by the flow chart of FIG. 4 is started by the control device 28 when the START/STOP button 48 is operated to supply a START signal to the control device 28.

The control of the control device 28 or the CPU 30 begins with an initial step (not shown) where the control device 28 clears a timer, t, to zero (t=0). Then, at Step S1 of FIG. 4, the control device 28 switches the selector valve 16 to its inflation position and operates the air pump 18, so that the air pressure Pc in the inflatable cuff 10 is quickly increased.

At Step S2, the control device 28 judges whether the cuff pressure Pc has been increased up to the predetermined target value $P_{CM}$ (e.g., 180 mmHg). Steps S1 and S2 are repeated and the cuff pressure Pc is increased, until a positive judgment is made at Step S2.

Meanwhile, if a positive judgment is made at Step S2, the control goes to Step S3 to stop the air pump 18 and switch the selector valve 16 to its slow-deflation position, so that the cuff pressure Pc is slowly decreased at the predetermined low rate of 3 mmHg/sec.

Step S3 is followed by Step S4 to determine, based on variation of respective amplitudes of respective heartbeat-synchronous pulses of the pulse wave represented by the pulse-wave signal SM supplied from the pulse-wave filter circuit 24 during the slow deflation of the cuff 10, a systolic blood-pressure value $BP_{SYS}$, a mean blood-pressure value $BP_{MEAN}$, and a diastolic blood-pressure value $BP_{DIA}$ of the female subject, according to well-known oscillometric BP determining algorithm.

At Step S5, the control device 28 calculates, while the cuff pressure Pc is slowly decreased at Step S3, i.e., before one or more blood-pressure values are determined at Step S4, a change rate, $d_{SU}$, of a magnitude of a current data point $SU_{t=n}$ of the labor-pain signal SU. The change rate $d_{SU}$ may be calculated by dividing the magnitude of the current data point of the labor-pain signal SU by the magnitude of the preceding data point $SU_{t=n-1}$ of the signal SU.

Step S5 is followed by Step S6. Steps S5 and S6 correspond to the measurement-abnormality judging means 60. At Step S6, the control device 28 judges whether the change rate $d_{SU}$ of the labor-pain signal SU, calculated at Step S5, falls within a reference range of 1± a predetermined reference value α (>0), and thereby judges whether the labor-pain signal SU falls within the reference range $R_B$ around the base line L. If a negative judgment is made at Step S6, that is, if the labor-pain signal SU does not fall within the reference range $R_B$, it can be estimated that no accurate blood pressure values would be obtained because of the labor pains felt by the female subject. Accordingly, the control of the control device 28 goes to Step S7 to cease the current BP measurement by switching the selector valve 16 to its quick-deflation position and thereby quickly deflating the cuff 10.

On the other hand, if a positive judgment is made at Step S6, the control device 28 continues the current BP measurement of the BP measuring means 50, and goes to Step S8 to judge whether the current BP determination has been finished, by judging whether the diastolic blood-pressure value $BP_{DIA}$ of the subject has been determined. The diastolic blood-pressure value $BP_{DIA}$ is last determined according to the oscillometric BP determining algorithm employed at Step S4. Steps S4 to S6 and S8 are repeated until a positive judgment is made at Step S8, and the oscillometric BP determining algorithm is continued.

Meanwhile, if a positive judgment is made at Step S8, the control goes to Step S9 to switch the selector valve 16 to its quick-deflation position and thereby quickly deflate the cuff 10. Thus, the current BP measurement is ended. Therefore, Steps S1 to S4 and S7 to S9 correspond to the BP measuring means 50.

Step S9 is followed by Step S10 to clear the timer t to zero (t=0), and then by Step S11 to operate the display device 36 to display the thus determined systolic, mean, and diastolic blood-pressure values $BP_{SYS}$, $BP_{MEAN}$, $BP_{DIA}$ of the female subject.

At Step S12, the control device 28 adds one to the timer t (t→t+1) and, at Step S13, the control device 28 calculates a change rate $d_{SU}$ of the magnitude of a current data point of the labor-pain signal SU in the same manner as employed at Step S5.

Step S13 is followed by Step S14 to judge whether the change rate $d_{SU}$ determined at Step S13 is not greater than the predetermined reference value α, i.e., whether the labor-pain signal SU falls within the reference range $R_B$. As described above, the BP measurement is performed during the no-pain period $T_A$. Therefore, a positive judgment is made at Step S14 immediately after the end of BP measurement. Then, the control of the control device 28 goes to Step S18. Step S14 should be repeated until the next BP measurement is started. However, if the female subject feels labor pains a certain time after the end of the last BP measurement, a negative judgment is made at Step S14.

Steps S6 and S7 or Step S14 is followed by Step S15 corresponding to the labor-pain-period-relating-information determining means 56. At Step S15, the control device 28 determines, as the non-pain period $T_A$, a time duration between a time when the last negative judgment is made at Step S14 and a time when the current negative judgment is made at Step S6 or S14, that is, a time duration during which positive judgments have been continuously made at Step S14.

Step S15 is followed by Step S16 to judge whether the non-pain period $T_A$ determined at Step S15 is shorter than a predetermined reference period $T_{A0}$. If a negative judgment is made at Step S16, Steps S12 and the following steps are repeated. On the other hand, if a positive judgment is made at StepS16, that is, if the non-pain period $T_A$ has shortened, the control goes to Step S17 to change or shorten the predetermined BP-measurement period $T_{B1}$ (e.g., 30 minutes) to a shorter period $T_{B2}$ (e.g., 10 minutes). Steps S16 and S17 correspond to the measurement-period shortening means 58. Then, the control of the control device 28 goes back to Step S12 and the following steps.

On the other hand, if a positive judgment is made at Step S14, the control goes to Step S18 to judge whether a time t measured by the timer t has exceeded the BP-measurement period $T_{B1}$ or $T_{B2}$. If a negative judgment is made at Step S18, the control goes back to Step S12 and the following steps. On the other hand, if a positive judgment is made at Step S8, the control goes back to Step S1 and the following steps to measure automatically one or more blood-pressure values of the female subject. More specifically described, at Step S14 it is judged that the labor-pain signal SU falls within the reference range $R_B$, and at Step S18 it is judged that the time t measured by the timer t has exceeded the BP-measurement period $T_{B1}$ or $T_{B2}$. Thus, Steps S10, S12–S14, and S18 correspond to the first BP-measurement starting means 54. In addition, when a positive judgment is made at Step S14 after a negative judgment is made at Step S6 during one or first BP measurement, another or second BP measurement is started at Step S18 since the time t measured by the timer t has already exceeded the BP-measurement period $T_{B1}$ or $T_{B2}$ before the negative judgment is made at Step S6. Thus, Steps S13 and S14 correspond to the second BP-measurement starting means 62.

It emerges from the foregoing description that in the present embodiment the first BP-measurement starting means 54 (Steps S10, S12–14, S18) operates the BP measuring means 50 (Steps S1 to S4 and S7 to S9) to start a BP measurement, only when the labor-pain signal SU supplied from the tocodynamometer 38 falls within the reference range $R_B$. When labor-pain signal SU falls within the reference range $R_B$, the female subject does not feel any labor pains in a no-pain period $T_A$. Thus, the present BP measuring apparatus 8 starts a BP measurement in the non-pain period $T_A$, it can measure one or more accurate blood-pressure values of the female subject.

In addition, in the present embodiment, the measurement-period shortening means 58 (Steps S16 and S17) shortens the predetermined BP-measurement period $T_{B1}$ to the shorter period $T_{B2}$, when the non-pain period $T_A$ becomes shorter than the reference period $T_{A0}$. That is, while the non-pain period or periods $T_A$ are shorter than the reference period $T_{A0}$, the present BP measuring apparatus 8 measures one or more blood-pressure values of the female subject at the shorter period $T_{B2}$. Thus, the present apparatus 8 can quickly detect any abnormal tendency of the subject.

Moreover, in the present embodiment, the measurement-abnormality judging means 60 (Step S6) judges, when the labor-pain signal SU goes out of the reference range $R_B$ during the current BP measurement, that the current BP measurement is abnormal. In this case, after the labor-pain signal SU has changed to fall within the reference range $R_B$, the second BP-measurement starting means 62 (Steps S13 and S14) operates the BP measuring means 50 to start another BP measurement. Thus, the present BP measuring apparatus can measure one or more accurate blood-pressure values BP of the subject.

While the present invention has been described in its preferred embodiment by reference to the drawings, it is to be understood that the invention may otherwise be embodied.

For example, in the illustrated embodiment, a BP measurement is started immediately after it is judged at Step S18 of FIG. 4 that the time measured by the timer t has exceeded the BP-measurement period $T_{B1}$ or $T_{B2}$. However, it is possible to insert, after Step S18, a step where the control device 28 judges whether it is immediately after the end of a plateau of the labor-pain signal SU, i.e., the end of a labor-pain duration. If a positive judgment is made, it is possible to start the BP measurement a predetermined time after the end of labor-pain duration.

In addition, in the flow chart of FIG. 4, Steps S5 and S6 are provided before Step S8, so that Steps S5 and S6 are repeatedly carried out, in each BP measurement, to find an abnormality of the BP measurement. However, Steps S5 and S6 may be provided after Step S8, so that Steps S5 and S6 are carried out one time, after each BP measurement, to find an abnormality of the BP measurement.

In the illustrated embodiment, the labor-pain signal SU is detected by an external method, i.e., by the tocodynamometer 38 of a type which is externally worn on the abdomen of the female subject. However, a labor-pain signal of the female subject may be detected by an internal method, e.g., by measuring an amniotic-fluid pressure, or a fetal/parturient-canal pressure, of the subject.

In the illustrated embodiment, the BP measuring means 50 measures one or more blood-pressure values BP of the female subject according to the so-called oscillometric method. However, the BP measuring means 50 may be replaced with one which measures one or more blood-pressure values BP of the female subject according to a so-called Korotkoff-sound method in which respective values of the cuff pressure Pc at the times when Korotkoff sounds are first and last detected are determined as systolic and diastolic blood-pressure values of the subject.

It is to be understood that the present invention may be embodied with other changes, improvements and modifications that may occur to one skilled in the art without departing from the spirit and scope of the invention.

What is claimed is:

1. An apparatus for automatically measuring a blood pressure of a female subject, comprising:
    a blood-pressure measuring device which includes an inflatable cuff adapted to apply a pressing force to a body portion of the subject and automatically measures, by changing the pressing force of the cuff, a blood pressure of the female subject at a predetermined measurement period;
    a labor-pain-signal detecting device which detects, from the female subject, a labor-pain signal which changes in relation to a labor pain of the subject;
    a first blood-pressure-measurement starting means for operating the blood-pressure measuring device to start a blood-pressure measurement, when the predetermined measurement period has elapsed and when the labor-pain signal detected by the labor-pain signal detecting device falls within a reference range;
    a labor-pain-period-relating-information determining means for determining, based on the labor-pain signal detected by the labor-pain detecting device, labor-pain-period-relating information relating to a labor-pain period at which the female subject periodically feels a labor pain; and
    a measurement-period shortening means for shortening the predetermined measurement period, when the determined labor-pain-relating information indicates that the labor-pain period of the subject has shortened.

2. An apparatus according to claim 1, further comprising:
    an abnormality judging means for judging, when the labor-pain signal detected by the labor-pain-signal detecting device does not fall within the reference range when the blood-pressure measuring device is performing a first blood-pressure measurement, that the first blood-pressure is abnormal; and
    a second blood-pressure-measurement starting means for operating the blood-pressure measuring device to start a second blood-pressure measurement when the labor-pain signal detected by the labor-pain-signal detecting device has changed to fall within the reference range after the abnormality judging means has judged that the first blood-pressure measurement is abnormal.

3. An apparatus according to claim 2, wherein the abnormality judging means comprises means for stopping the first blood-pressure measurement judged as being abnormal.

4. An apparatus according to claim 1, wherein the labor-pain-signal detecting device comprises a tocodynamometer which is adapted to be held in contact with an abdomen of the female subject and which detects a pressure increase which is produced when a uterus of the subject contracts.

5. An apparatus according to claim 2, wherein the labor-pain-period-relating-information determining means comprises means for determining, as the labor-pain-period-relating information, the labor-pain at which the female subject periodically feels the labor pain.

6. An apparatus according to claim 2, wherein the labor-pain-period-relating-information determining means comprises means for determining, as the labor-pain-period-relating information, a no-pain duration during which the labor-pain signal detected by the labor-pain-signal detecting device falls within the reference range.

7. An apparatus according to claim 1, wherein the measurement-period shortening means comprises judging means for judging whether the labor-pain period of the subject indicated by the labor-pain-period-relating information determined by the labor- pain-period-relating-information determining means is shorter than a reference value; and shortening means for shortening the predetermined measurement period when the judging means makes a positive judgment.

8. An apparatus according to claim 2, wherein the measurement-period shortening means comprises shortening means for shortening the predetermined measurement period as a first predetermined period to a second predetermined period shorter than the first predetermined period.

* * * * *